(12) United States Patent
Shanahan et al.

(10) Patent No.: US 8,783,786 B2
(45) Date of Patent: Jul. 22, 2014

(54) CUTTER ASSEMBLY FOR TUNNEL BORING MACHINE WITH PRESSURE COMPENSATION

(75) Inventors: Aaron J. Shanahan, Seattle, WA (US); Stephen M. Smading, Renton, WA (US); Timothy A. Lang, Seattle, WA (US); Zachary J. Box, Renton, WA (US); Brian B. Khalighi, Bellevue, WA (US); Brad D. Grothen, Renton, WA (US); Carl E. Lenaburg, Tacoma, WA (US); Jay M. McNeeley, Maple Valley, WA (US); Shinichi Konda, Issaquah, WA (US)

(73) Assignee: The Robbins Company, Solon, OH (US)

( * ) Notice: Subject to any disclaimer, the term of this patent is extended or adjusted under 35 U.S.C. 154(b) by 162 days.

(21) Appl. No.: 13/397,997

(22) Filed: Feb. 16, 2012

(65) Prior Publication Data

US 2012/0212034 A1   Aug. 23, 2012

Related U.S. Application Data

(60) Provisional application No. 61/444,081, filed on Feb. 17, 2011.

(51) Int. Cl.
*E21D 9/10* (2006.01)

(52) U.S. Cl.
CPC ........................................ *E21D 9/104* (2013.01)
USPC .............................. 299/106; 299/110; 299/58

(58) Field of Classification Search
CPC ............................. E21D 9/1006; E21D 9/104
USPC ...................................... 299/55, 58, 106, 110
See application file for complete search history.

(56) References Cited

U.S. PATENT DOCUMENTS

| 3,985,366 A | 10/1976 | Plouzek |
|---|---|---|
| RE31,511 E | 1/1984 | Spencer |

(Continued)

FOREIGN PATENT DOCUMENTS

JP         08-270371         10/1996

OTHER PUBLICATIONS

International Search Report and Written Opinion mailed Oct. 8, 2012, issued in corresponding International Application No. PCT/US2012/025478, filed Feb. 16, 2012, 6 pages.

*Primary Examiner* — David Bagnell
*Assistant Examiner* — Michael Goodwin
(74) *Attorney, Agent, or Firm* — Christensen O'Connor Johnson Kindness PLLC

(57) ABSTRACT

A pressure-compensated cutter assembly for a tunnel boring machine includes a shaft a cutter ring assembly rotatably mounted on the shaft, and first and second end retainers non-rotatably attached to the shaft. Rotary seal groups, immersed in lubricant, provide a moving seal between the rotating cutter ring assembly and the end retainers. A movable piston member is exposed to ambient pressures, and contacts the lubricant, such that increasing ambient pressure will increase the lubricant pressure, thereby keeping the pressure differential across the seal small. In one embodiment, the piston is a floating retainer portion. In another embodiment, the piston is an annular piston, and in another embodiment, the piston is a plurality of smaller pistons disposed in the first retainer.

20 Claims, 9 Drawing Sheets

(56) References Cited

U.S. PATENT DOCUMENTS

| | | | |
|---|---|---|---|
| 4,784,438 A | 11/1988 | Fikse | |
| 4,825,964 A * | 5/1989 | Rives | 175/371 |
| 5,203,614 A | 4/1993 | Robbins | |
| 5,234,064 A | 8/1993 | Lenaburg | |
| 5,520,361 A | 5/1996 | Lee | |
| 5,577,565 A * | 11/1996 | Kocab et al. | 175/228 |
| 5,598,895 A | 2/1997 | Anderson | |
| 5,626,201 A * | 5/1997 | Friant et al. | 175/365 |
| 5,899,282 A | 5/1999 | Brussmann | |
| 5,904,211 A * | 5/1999 | Friant et al. | 175/228 |
| 5,961,185 A | 10/1999 | Friant | |
| 6,131,676 A * | 10/2000 | Friant et al. | 175/371 |
| 7,014,271 B2 | 3/2006 | Burger | |
| 7,832,960 B2 | 11/2010 | Home | |
| 2008/0202818 A1 | 8/2008 | McManus | |
| 2009/0079256 A1* | 3/2009 | Oertley et al. | 299/55 |
| 2009/0297273 A1 | 12/2009 | Lindbergh | |

\* cited by examiner

CUTTER ASSEMBLY FOR TUNNEL BORING MACHINE WITH PRESSURE COMPENSATION

CROSS-REFERENCE TO RELATED APPLICATION

This application claims the benefit of U.S. Provisional Application No. 61/444,081, filed on Feb. 17, 2011, which is hereby incorporated by reference in its entirety.

BACKGROUND

A tunnel boring machine ("TBM") is an excavation apparatus that is typically used to bore a tunnel through soil and rock strata. A conventional TBM produces a smooth circular tunnel wall, typically with minimal collateral disturbance. A breakthrough that made TBMs efficient and reliable was the invention of the rotating head with rotatable cutter assemblies, developed by James S. Robbins. Initially, Robbins' TBM used strong spikes fixedly mounted to the rotating head, but the spikes would break frequently. He discovered that by replacing these grinding spikes with longer lasting rotating disc cutter assemblies this problem was significantly reduced.

Modern TBMs therefore typically employ rotating heads with disc cutter assemblies that are rotatably mounted to the head. The head is urged with significant force against the target surface such that at least some of the cutter assemblies engage the surface. As the head rotates, the cutters fractionate, crush, and/or loosen materials, which are transported away by the TBM. As the loosened material is removed, the TBM progresses to bore the tunnel.

Diverse ground conditions are encountered in the excavation of some tunnels. Sand, marl, limestone, clays, and chalk may all be expected. At times, several types of ground may be encountered simultaneously. The disc cutter assemblies typically must operate in extreme conditions and must function reliably under high loads. For example, the cutter disc or blade may exert in excess of 75,000 pounds force normal to a rock face.

The water table along a tunnel boring trajectory may also vary considerably. In some applications, TBMs encounter highly saturated and flowable materials. When encountering loose and/or saturated soil conditions, the hydrostatic pressures on the cutter assemblies can be significant. If dirt or other foreign matter gets into the cutter bearing assembly, the cutter assembly may seize, requiring the user to repair or replace the cutter assembly before continuing. Cutter assemblies are provided with a durable and rugged seal to avoid the incursion of dirt into the bearing assembly. However, if the hydrostatic loads across the seals become sufficiently high, the seals may be breached.

There remains a need for improved sealing mechanisms to prevent the incursion of dirt and other foreign matter into the cutter assemblies of tunnel boring machines operating in conditions of high hydrostatic pressures.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A cutter assembly for a tunnel boring machine that is suitable for use, for example, in highly saturated soils and at high ambient pressures, is disclosed. The cutter assembly includes a shaft, a cutter ring assembly rotatably mounted to the shaft, and first and second oppositely disposed end retainer non-rotatably attached to the shaft. Seal groups, for example, mechanical face seals or duo-cone seals, provide sealing between rotating components and non-rotating components, and available volume in the cutter assembly is filled with a lubricant, for example, oil. The magnitude of the pressure across the seal groups when the cutter assembly is operated at depth is reduced by incorporating a movable piston portion into at least one of the end retainers. The movable piston portion has an outer surface that is exposed to the local ambient pressure and is configured to increase the lubricant pressure in response to increases in the ambient pressure. The cutter ring assembly may be formed as a unitary structure, or may be formed with a hub with one or more cutter rings removably attached.

In an embodiment, at least one of the end retainers includes a fixed retainer having a pressure port that is in fluid communication with the lubricant, and a floating retainer that slidably engages the fixed retainer to define a gap filled with the lubricant. The floating retainer may include an outer wall that is configured to receive the fixed retainer and an inner wall that is configured to slidably engage an annular channel in the fixed retainer.

In an embodiment, at least one of the end retainers includes an outwardly facing annular channel with a pressure port extending through the end retainer, and a ring-shaped piston that is slidably disposed in the channel. The lubricant fills the volume between the channel and the piston. The ring-shaped piston is exposed to a local ambient pressure such that increasing ambient pressure will increase the lubricant pressure. The channel may include a plurality of pressure ports.

In an embodiment, at least one of the end retainers has a plurality of cylindrical recesses and corresponding ports that extend from the recesses through the end retainer. A piston is slidably disposed in each recess, and the volume between each piston and port is filled with the lubricant. In one embodiment, an extendable seal is provided over each recess.

In an embodiment, a pressure-compensated cutter assembly for a tunnel boring machine includes a shaft, a cutter ring rotatably mounted on the shaft, a first end retainer and a second end retainer non-rotatable attached to the shaft, seal groups bathed in a lubricant and disposed between cutter ring and the first and second end retainers, and a piston means incorporated into at least one of the end retainers configured to transmit at least a portion of the external ambient pressure into the lubricant.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
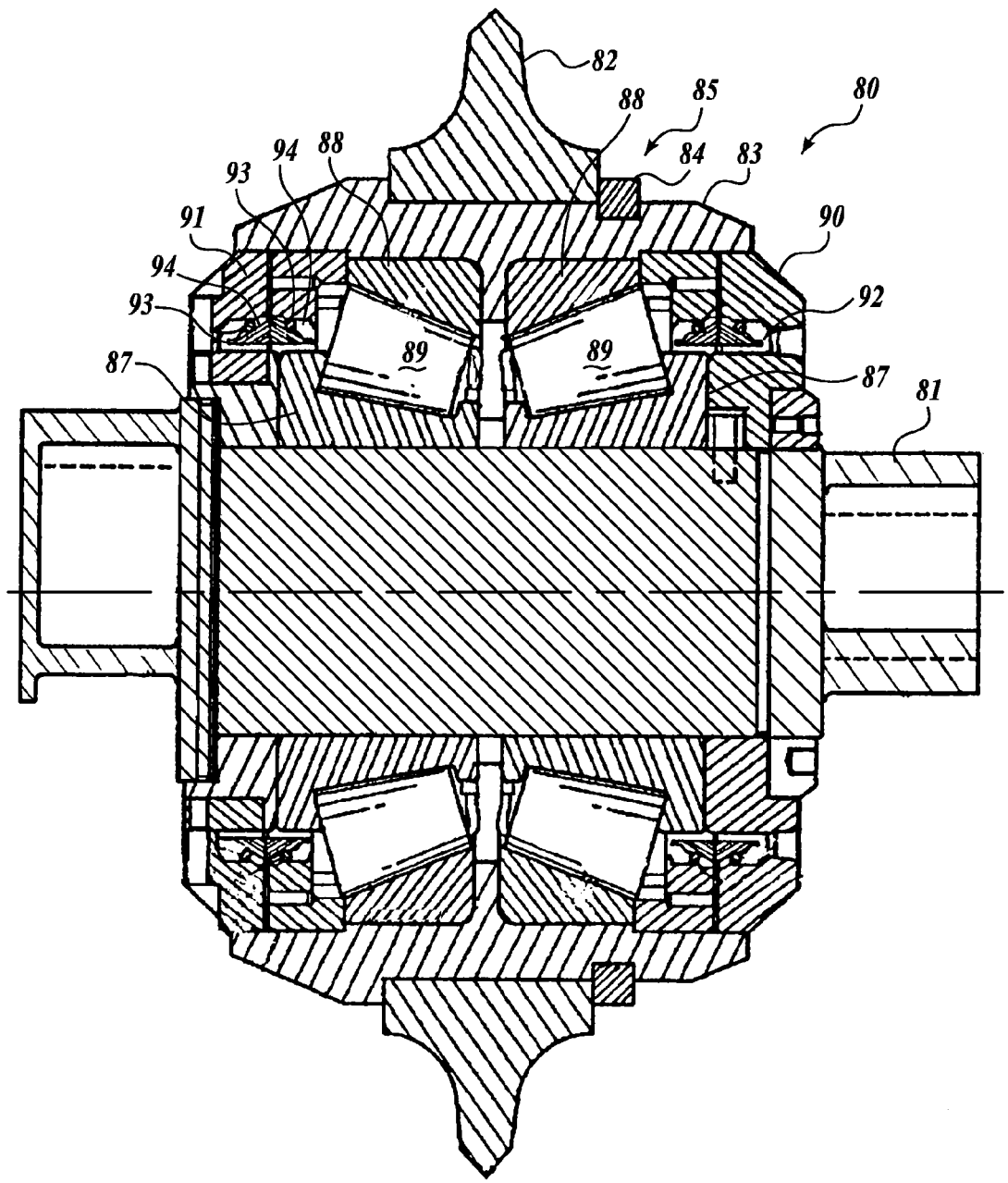
FIG. 1 is a cross-sectional front view of a prior art cutter assembly.

FIG. 1 is a cross-sectional view of a prior art cutter assembly 80 for a tunnel boring machine. An exemplary tunnel boring machine is disclosed in U.S. Pat. No. 7,832,960, which is hereby incorporated by reference in its entirety.

The cutter assembly 80 includes a shaft 81 that is configured to be fixedly attached to the TBM rotating head. An annular cutter ring 82 is attached to a hub 83 with a retainer ring 84, to form a ring assembly 85. The ring assembly 85 is rotatably mounted to the shaft 81 with a pair of bearing assemblies comprising an inner bearing race 87, an outer bearing race 88, and a plurality of tapered roller bearings 89. A pair of end retainers 90, 91 are disposed on either side of the hub 83. During operation, the ring assembly 85 is rotatable about the shaft 81, and the end retainers 90, 91 are fixed to the shaft 81.

A rotary seal group 92 is provided at the interface between each of the end retainers 90, 91 and the ring assembly 85. Rotary seal groups for cutter assemblies are typically mechanical face seals, also referred to as duo-cone seals. A particular duo-cone seal assembly is discloses in U.S. Pat. No. 3,985,366, which is hereby incorporated by reference in its entirety. Mechanical face seals were developed for protecting equipment working in the most adverse conditions, and comprise a pair of annular metal seal rings 93 and a pair of elastic toric members 94 (e.g., O-rings). The outer metal seal ring 93 engages the associated end retainer 90 or 91 through a toric member 94 and is fixed, and the associated inner metal seal ring 93 engages the ring assembly 85 through a toric member 94. The two associated metal seal rings 93 abut to form a moving seal interface. Typically the available interior volume between the end retainers 90, 91 is filled with a lubricant, e.g., oil or grease.

The rotary seal groups 92 provide a seal to prevent the incursion of dirt that could damage or destroy the bearing assemblies. Mechanical face seals were specifically designed to provide reliable sealing protection in very harsh environments. However, if the cutter assembly 80 is used in an environment having high hydrostatic pressure loading, for example, at significant depths in a saturated media, the external pressure may overcome the rotary seal groups 92, which can result in failure of the cutter assembly.

Figure 2:
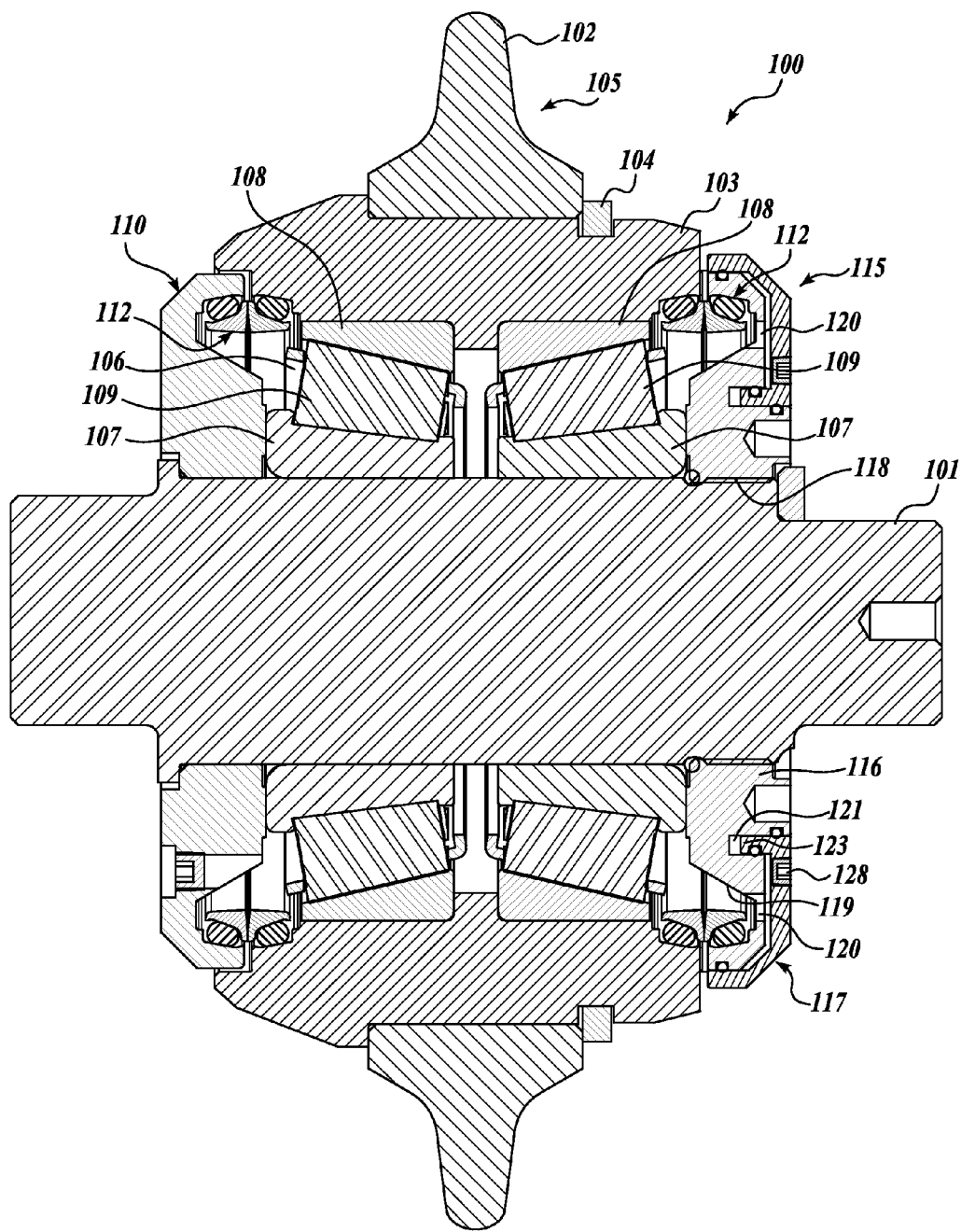
FIG. 2 is a cross-sectional front view of a first embodiment of a pressure-compensated cutter assembly in accordance with the present invention.

FIG. 2 is a cross-sectional view of a pressure-compensated cutter assembly 100 in accordance with the present invention. The pressure-compensated cutter assembly 100 is similar in many aspects to the prior art cutter assembly 80 discussed above. A ring assembly 105 is shown, including an annular cutter ring 102 mounted on a hub 103 and secured with a retainer ring 104. Other constructions of the ring assembly are contemplated. For example, in alternative embodiments the cutter ring and hub may be formed as a single, unitary component, rather than as the currently preferred assembly. The ring assembly 105 is rotatably mounted on a shaft 101 with left and right bearing assemblies, each bearing assembly comprising an inner race 107, an outer race 108, and a plurality of tapered roller bearings 109 captured in a bearing cage 106. A pair of rotary seal groups 112 comprising mechanical face seals provide protection for the bearing assemblies.

A conventional end retainer 110 is attached to the shaft 101 on one side (on the left side in FIG. 2), and a pressure-compensating retainer assembly 115 is attached to the shaft 101 on the opposite side (on the right in FIG. 2). In this embodiment, the pressure-compensating end retainer 115 includes a fixed retainer 116 and a floating retainer 117 which functions as a piston to increase the pressure of lubricant in the cutter assembly 100, as discussed below.

The fixed retainer 116 is fixed to the shaft 101, and the floating retainer 117 slidably engages the fixed retainer 116. In the current embodiment, the fixed retainer 116 has a threaded center aperture 118 that engages corresponding threads on the shaft 101.

Figure 3:
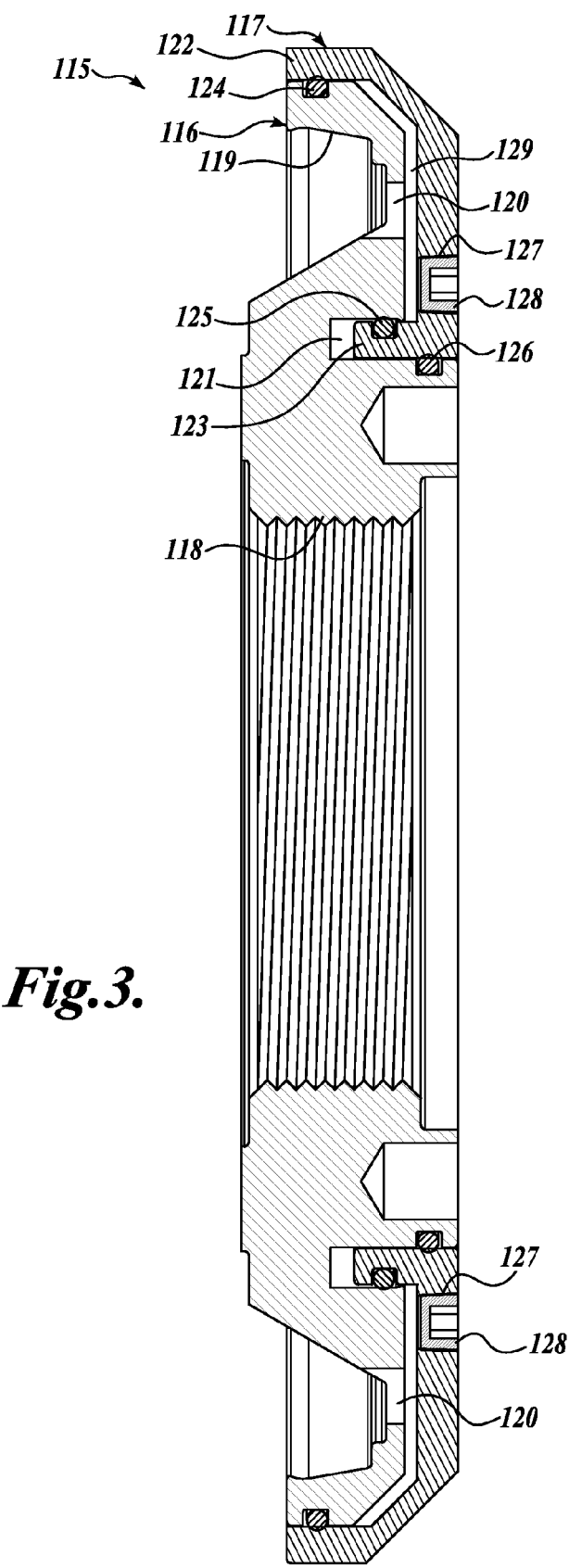
FIG. 3 is a cross-sectional side view of the pressure-compensating retainer assembly for the cutter assembly shown in FIG. 2.

Refer now also to FIG. 3, which shows a cross-sectional view of the pressure-compensating retainer assembly 115 in isolation. The fixed retainer 116 has a peripheral inner recessed portion 119 that is configured to engage the non-rotating portion of the rotary seal group 112. One or more apertures 120 are provided through the recessed portion 119. For example, in a current embodiment, four evenly-spaced apertures 120 are provided (two visible in FIG. 3). An external annular slot 121 is also provided at a radial location between the recessed portion 119 and the center aperture 118.

The floating retainer 117 is a generally annular ring having a U-shaped cross section with an outer wall 122 that is sized and positioned to slidably engage the outer perimeter of the fixed retainer 116, and an inner wall 123 that is sized and positioned to slidably engage the annular slot 121. A first O-ring 124 provides a seal between the floating retainer 117 outer wall 122 and the fixed retainer 116. A pair of O-rings 125, 126 provides a seal between the inner wall 123 and the fixed retainer 116 annular slot 121. One or more threaded apertures 127 through the floating retainer 117 provide a means for injecting a lubricant into a gap 129 between the fixed retainer 116 and the floating retainer 117. The threaded apertures 127 are closed with corresponding threaded plugs 128.

The operation of the pressure-compensated cutter assembly 100 can now be appreciated, recalling that the available volume in the cutter assembly 100 is also filled with the lubricant. When the hydrostatic pressure on the cutter assembly 100 increases, for example, when the boring operation encounters highly saturated ground at significant depths, the high hydrostatic pressure will cause the floating retainer 117 to move inwardly towards the fixed retainer 116, pressurizing the oil (or other lubricant) in the gap 129, and thereby pressurizing the volume behind the seal group 112. The pressure differential across the seal group 112 will therefore automatically remain small by the action of the floating retainer 117, and the risk of foreign matter incursion into the bearing assembly is greatly diminished.

Figure 4:
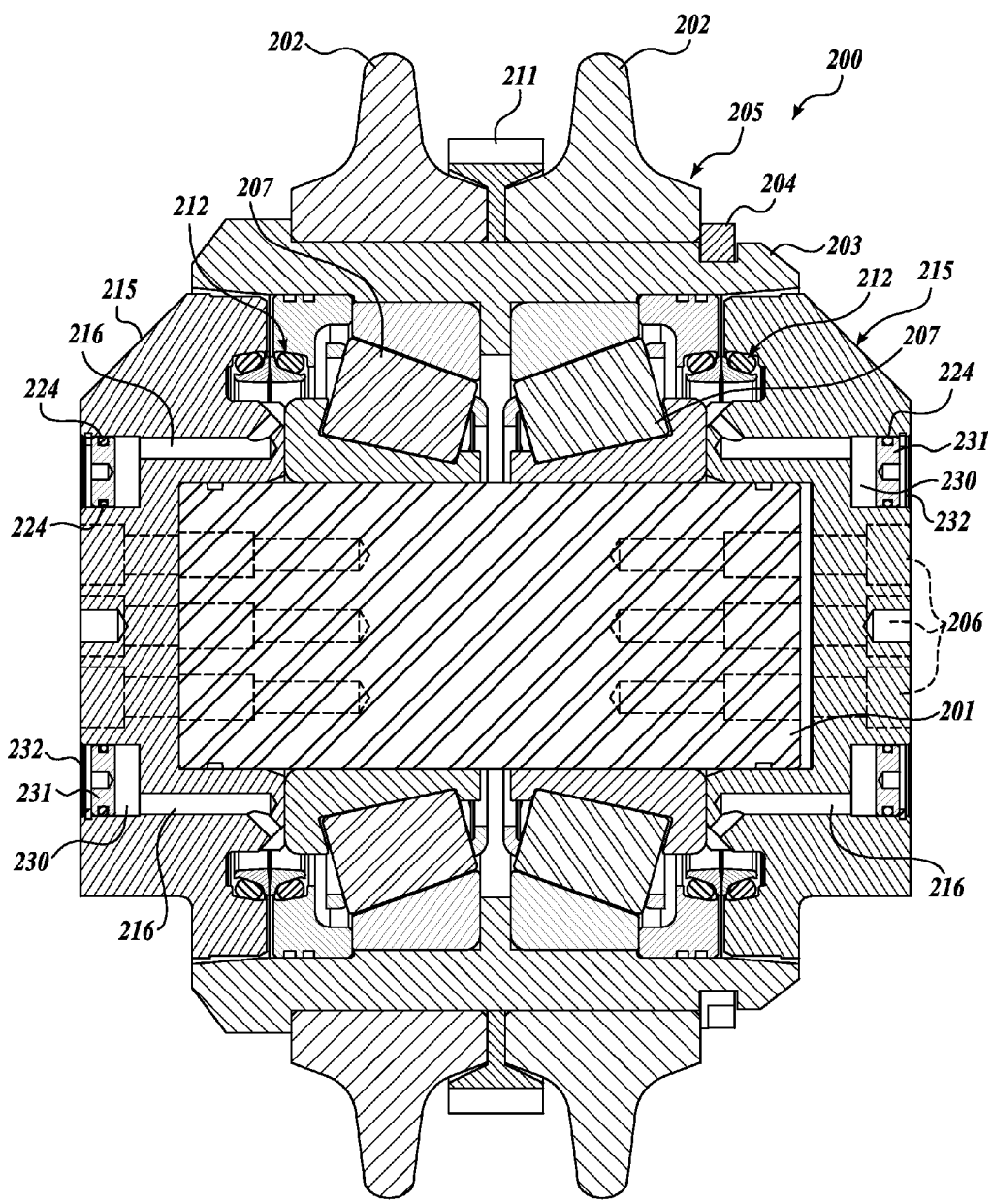
FIG. 4 is a cross-sectional front view of a second embodiment of a pressure-compensated cutter assembly in accordance with the present invention.
Figure 5:
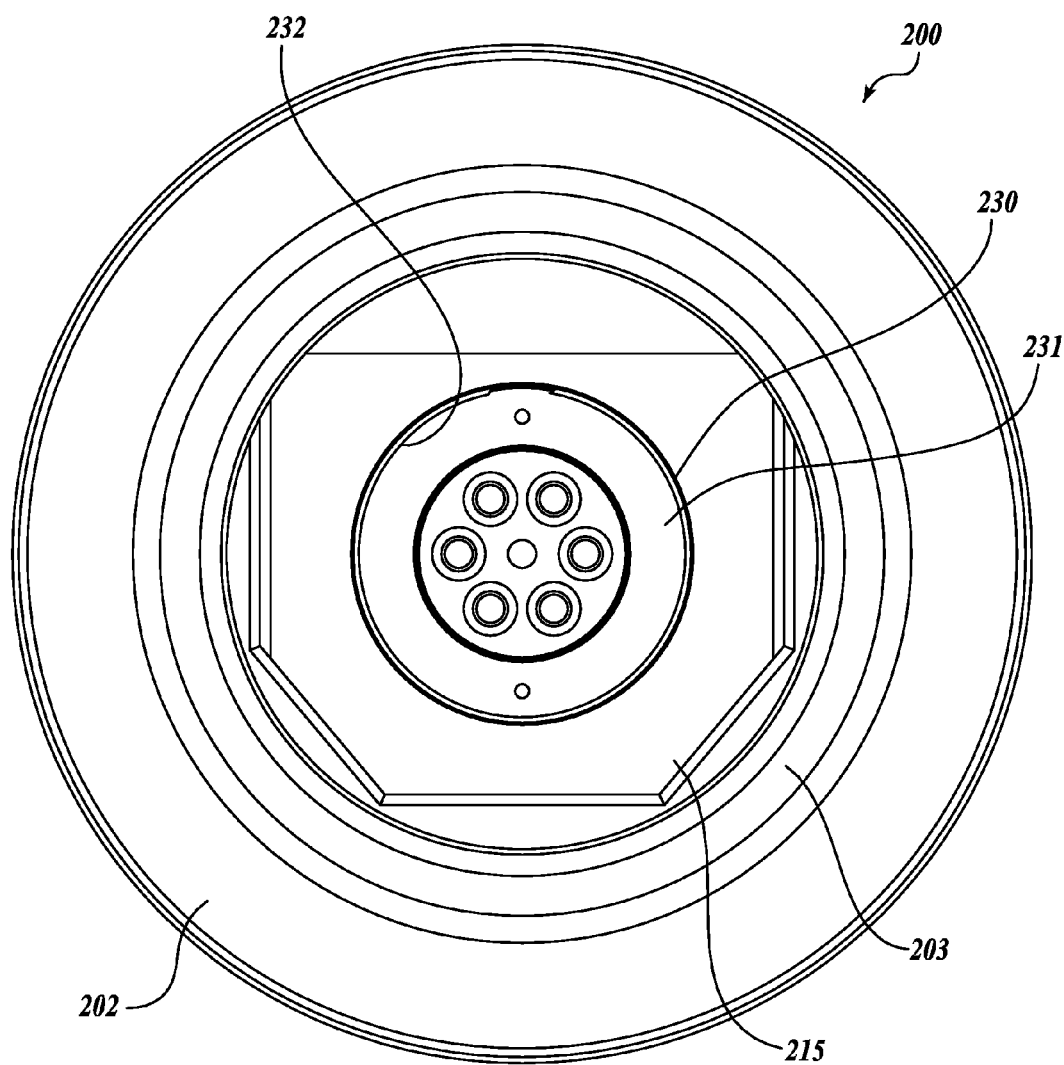
FIG. 5 is a side view of the cutter assembly shown in FIG. 4.
Figure 6:
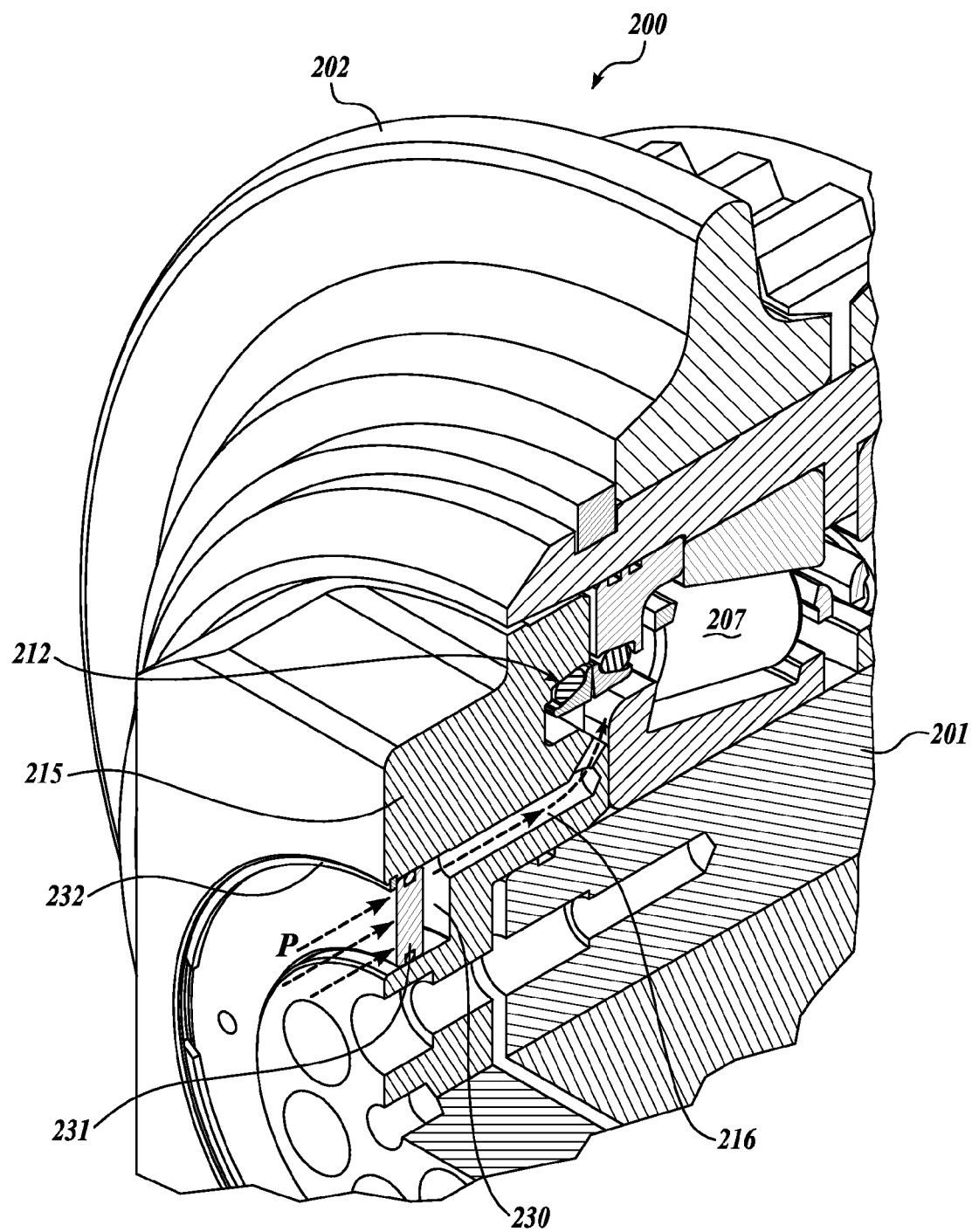
FIG. 6 is a detail cross-sectional view showing a close up of the pressure port for the cutter assembly shown in FIG. 4.

Another embodiment of a pressure-compensated cutter assembly 200 in accordance with the present invention is shown in FIGS. 4-6. FIG. 4 is a cross-sectional view of the cutter assembly 200, FIG. 5 is a side view of the cutter assembly 200, and FIG. 6 is a detail cross-sectional view showing a close up of the pressure port.

This exemplary embodiment illustrates a double disc cutter assembly 200 having two cutter rings 202 and a toothed spacer 211 mounted on a hub 203 and secured with a retainer ring 204. A bearing assembly 207, similar to the bearing assembly discussed above, rotatably couples the ring assembly 205 with a center shaft 201. Oppositely disposed pressure-compensating end retainers 215 are fixed to the shaft 201, for example the end retainers 215 may attach to the shaft 201 with bolts 206. A pair of rotary seal groups 212, similar to that disclosed above, provides a seal between the rotating components and the fixed components.

In this embodiment, the end retainers 215 each define an outwardly open annular channel 230. A plurality of ports 216 extend through the end retainer 215 from the annular channel 230 to the interior of the cutter assembly 200. An annular piston 231 is slidably disposed in the channel 230, and sealingly engages the walls of the annular channel 230 with O-rings 224. The annular piston 231 may be retained in the channel 230 with a C-clip 232 or the like.

As discussed above, the interior of the cutter assembly 200 is filled with a lubricant, for example oil. In this embodiment the ports 216 and the inward portion of the annular channel 230 are also filled with oil.

It will now be appreciated that if the cutter assembly encounters high hydrostatic pressure the external pressure P will tend to push the annular piston 231 inwardly, pressurizing the oil, and push through the ports 216, thereby pressurizing the region behind the rotary seal group 212 such that the pressure across the seal group 212 is approximately equalized. Therefore, the pressure differential across the seal group 212 will remain small by the action of the annular piston 231, and the risk of foreign matter incursion into the bearing assembly is greatly diminished.

Figure 7:
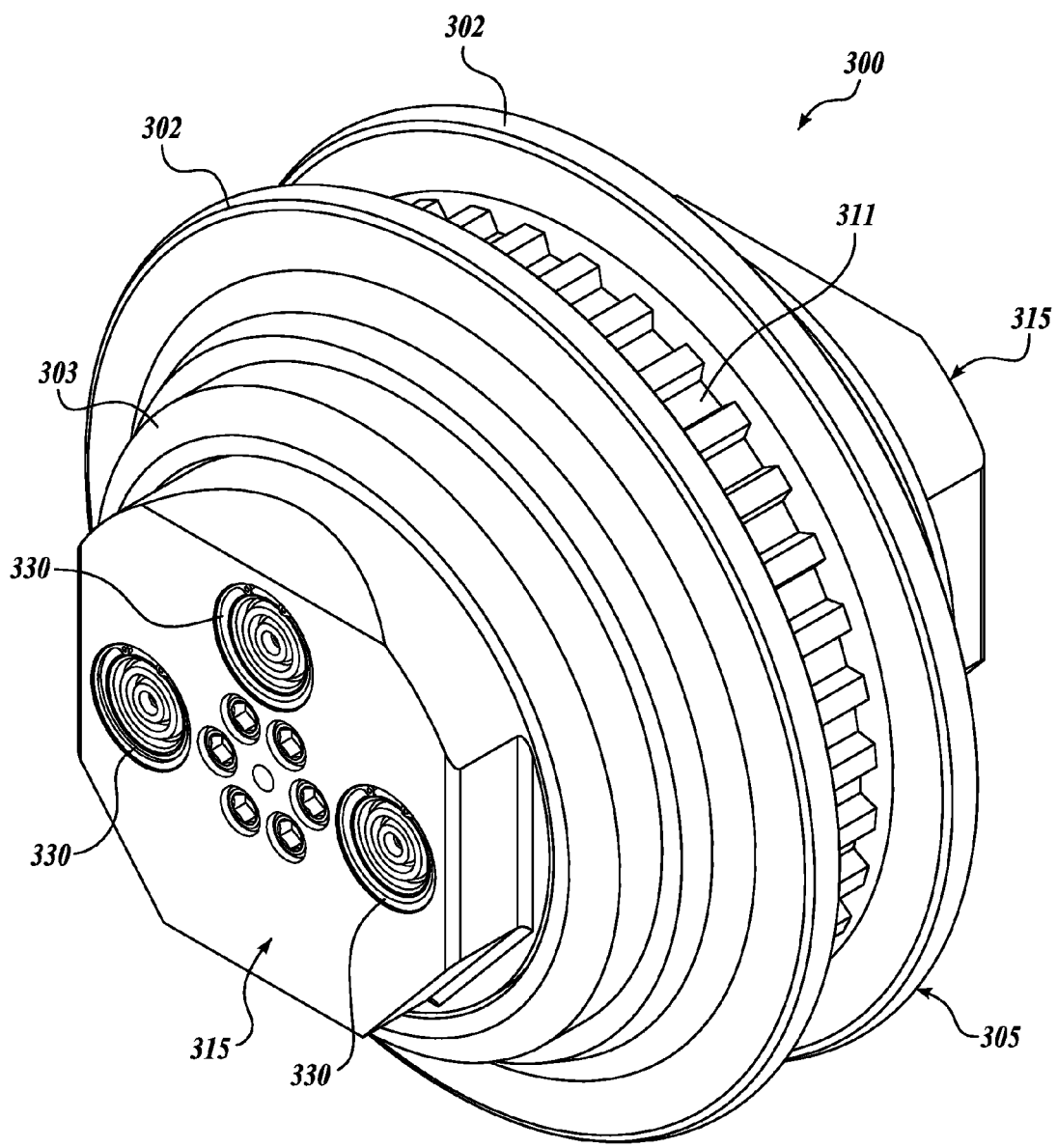
FIG. 7 is a perspective view of a third embodiment of a pressure-compensated cutter assembly in accordance with the present invention.
Figure 8:
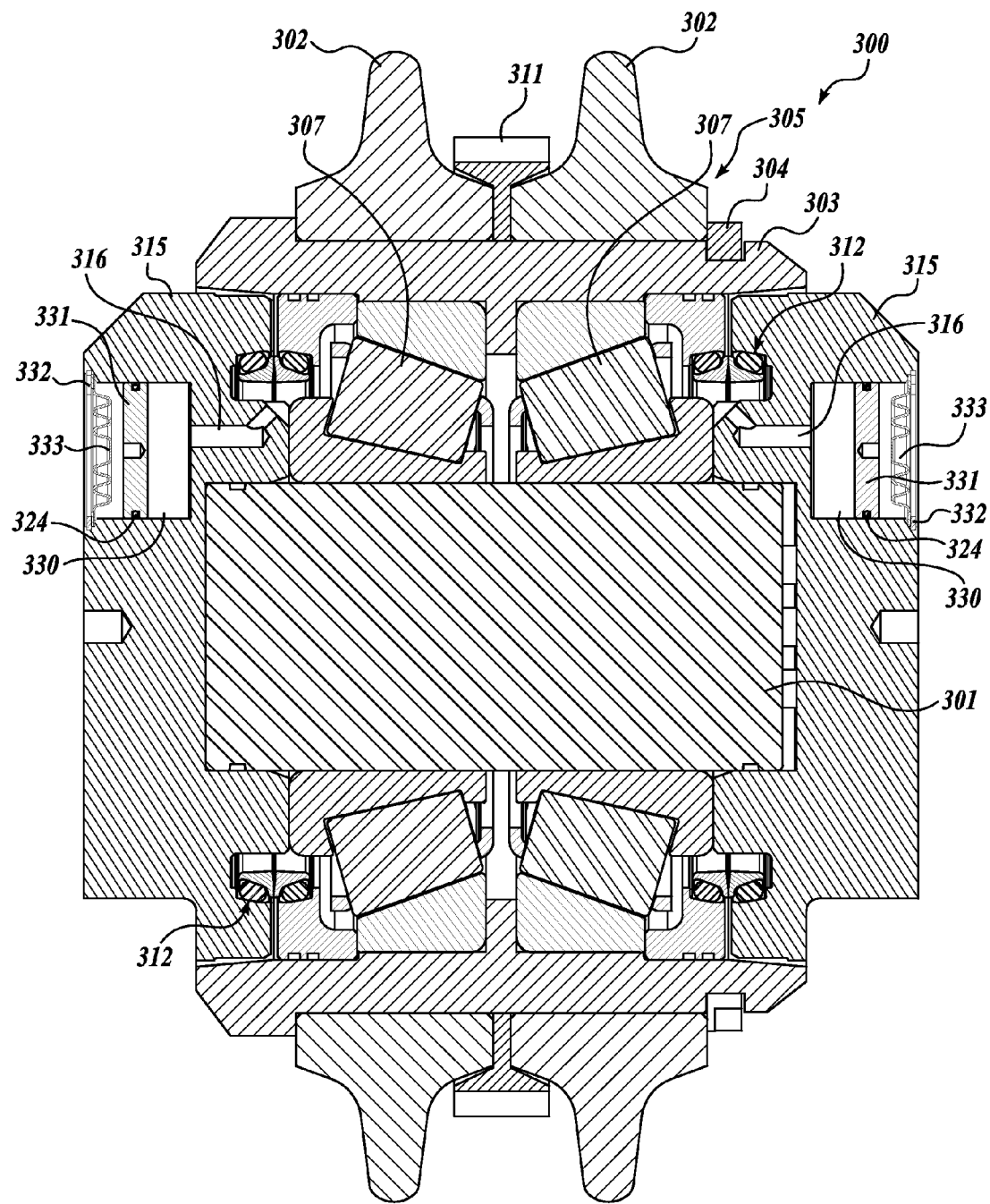
FIG. 8 is a cross-sectional front view of the cutter assembly shown in FIG. 7.
Figure 9:
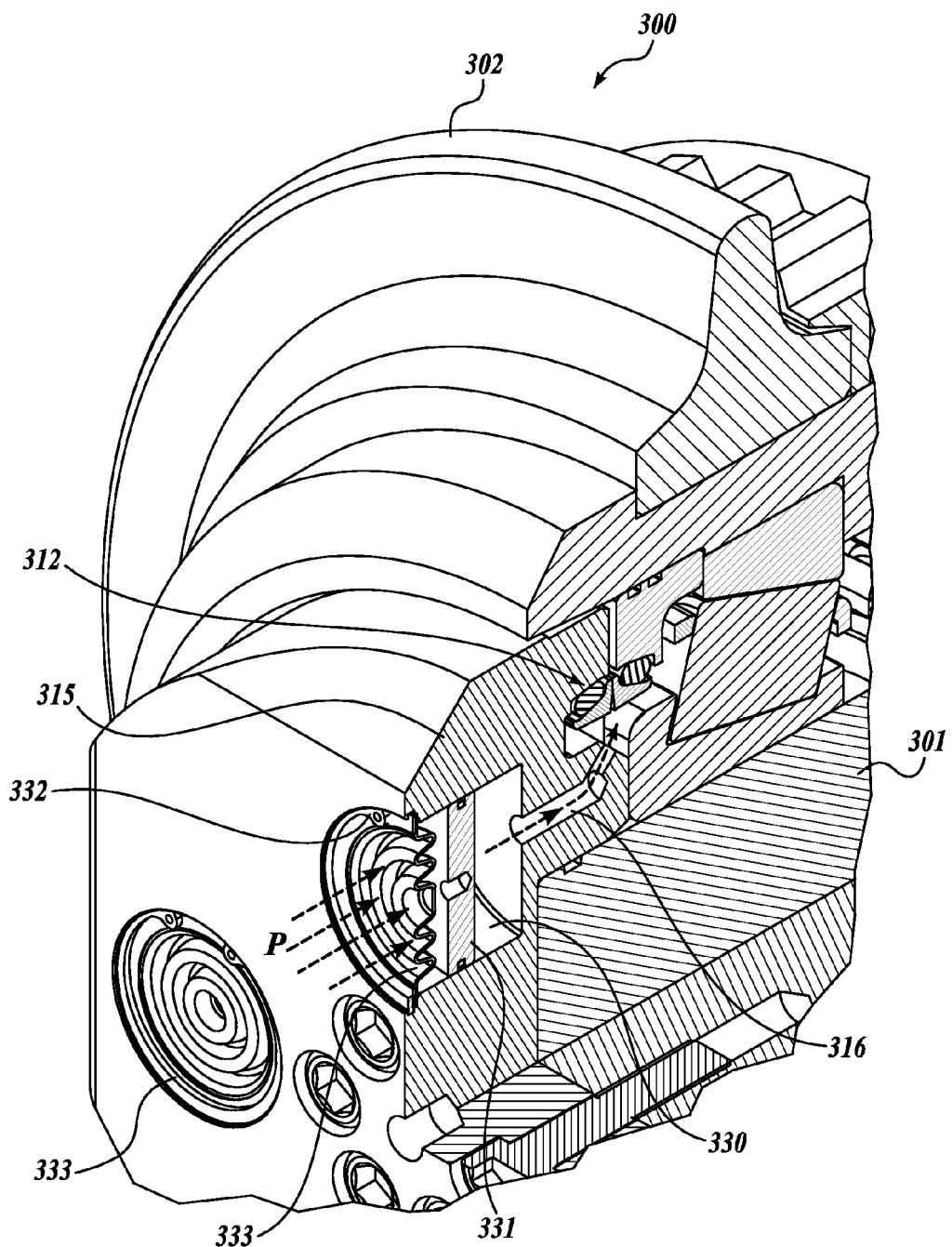
FIG. 9 is a detail cross-sectional view showing a piston and pressure port for the cutter assembly shown in FIG. 7.

Another embodiment of a pressure-compensated cutter assembly 300 in accordance with the present invention is shown in FIGS. 7-9. FIG. 7 is a perspective view of the cutter assembly 300, FIG. 8 is a cross-sectional view of the cutter assembly 300, and FIG. 9 is a detail cross-sectional view showing a close up of the pressure port.

The cutter assembly 300 is also a double disc cutter having two cutter rings 302 and a toothed spacer 311 mounted on a hub 303 with a retainer ring 304, similar to the cutter assembly 200 described above. A pair of tapered roller bearing assemblies 307 rotatably couples the ring assembly 305 with a center shaft 301. Oppositely disposed pressure-compensating end retainers 315 are also attached to the shaft 301. A pair of mechanical face seal rotary seal groups 312 provides a seal between the rotating ring assembly 305 and the fixed components.

In this embodiment, the end retainers 315 include a plurality of cylindrical recesses 330 on the outside face of each retainer 315 that connect to the interior of the cutter assembly 300 through associated ports 316. A floating disc-shaped piston 331 is disposed in each recess 330 and sealingly engages the cylindrical recess 330 through O-rings 324. A circularly pleated or otherwise extendable seal 333 protects the cylindrical recess 330 from dirt and other foreign matter. The seal 333 may be retained in the recess 330 with a C-clip 332 or the like.

As with the embodiments above, the cutter assembly 300 is filled with a lubricant, and the cylindrical recesses 330 are similarly filled with the lubricant, at least for the portion disposed inwardly from the associated piston 331. As indicated in FIG. 9, when the cutter assembly 300 is subject to external hydrostatic pressure P the pistons 331 will be urged inwardly, pressurizing the lubricant in the associated recess 330, thereby pressurizing the interior of the cutter assembly 300. The pressure in the interior of the cutter assembly 300 will therefore approximately equilibrate to the external hydrostatic pressure P.

Although the end retainers 315 are shown with three cylindrical recesses 330 in the current embodiment, it will be readily appreciated that more or fewer pressure-compensating mechanisms may be utilized.

Also, it will be appreciated that external expandable seals corresponding with the extendable seals 333 may be incorporated into the second disclosed embodiment 200 above with straightforward changes that would be apparent to persons of skill in the art.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A cutter assembly for a tunnel boring machine comprising:
    a shaft;
    a cutter ring assembly rotatably mounted on the shaft;
    a first end retainer attached to one end of the shaft and a second end retainer attached on an opposite end of the shaft, the first end retainer having a fixed retainer with a pressure port therethrough and a movable piston portion with an outer surface subject to a local hydrostatic pressure, the movable piston portion comprising a floating retainer that slidably engages the fixed retainer such that a gap is defined between the fixed retainer and the floating retainer that is in fluid communication with the pressure port;
    a first rotary seal group having a first portion engaging the cutter ring assembly and a second portion engaging the first end retainer; and
    a second rotary seal group having a first portion engaging the cutter ring assembly and a second portion engaging the second end retainer;
    such that the first rotary seal group is immersed in a lubricant that is in fluid communication with the port and fills the gap between the fixed retainer and the floating retainer such that the movable piston portion is configured to increase the pressure of the lubricant in response to an increase in the local hydrostatic pressure; and further
    wherein the fixed retainer further comprises an annular channel and an outer perimeter, and further wherein the floating retainer comprises an annular wall that slidably engages the annular channel and an outer wall that slidably engages the outer perimeter of the fixed retainer.

2. The cutter assembly of claim 1, wherein the floating retainer further comprises a through port to facilitate injecting lubricant into the gap and a plug that sealingly closes the through port.

3. The cutter assembly of claim 1, wherein the cutter ring assembly comprises a hub rotatably mounted to the shaft with tapered roller bearings and a cutter ring extending radially outwardly from the hub.

4. The cutter assembly of claim 1, where the first rotary seal group comprises a duo-cone seal.

5. A cutter assembly for a tunnel boring machine comprising:
    a shaft;
    a cutter ring assembly rotatably mounted on the shaft;
    a first end retainer attached to one end of the shaft and a second end retainer attached on an opposite end of the shaft, the first end retainer having a movable piston portion with an outer surface subject to a local hydrostatic pressure;
    a first rotary seal group having a first portion engaging the cutter ring assembly and a second portion engaging the first end retainer; and a second rotary seal group having a first portion engaging the cutter ring assembly and a second portion engaging the second end retainer;

wherein the first rotary seal group is immersed in a lubricant;

wherein the movable piston portion is configured to increase the pressure of the lubricant in response to an increase in the local hydrostatic pressure; and wherein the first end retainer comprises an outer surface defining an annular channel with at least one pressure port that extends from the annular channel through the first end retainer to provide fluid communication with an inner side of the first rotary seal group, and an annular piston slidably disposed in the annular channel and exposed to the hydrostatic pressure, and further comprising means for retaining the annular piston in the annular channel, wherein the annular channel volume between the annular piston and the pressure port is filled with the lubricant.

6. The cutter assembly of claim 5, wherein the at least one pressure port comprises a plurality of pressure ports.

7. The cutter assembly of claim 5, further comprising a retaining element disposed in the annular channel and operable to retain the annular piston in the annular channel.

8. The cutter assembly of claim 5, wherein the first rotary seal group comprises a duo-cone seal.

9. A cutter assembly for a tunnel boring machine comprising:
a shaft;
a cutter ring assembly rotatably mounted on the shaft;
a first end retainer attached to one end of the shaft and a second end retainer attached on an opposite end of the shaft, the first end retainer having a movable piston portion with an outer surface subject to a local hydrostatic pressure;
a first rotary seal group having a first portion engaging the cutter ring assembly and a second portion engaging the first end retainer; and
a second rotary seal group having a first portion engaging the cutter ring assembly and a second portion engaging the second end retainer;
wherein the first rotary seal group is immersed in a lubricant;
wherein the movable piston portion is configured to increase the pressure of the lubricant in response to an increase in the local hydrostatic pressure; and
wherein the first end retainer comprises a plurality of cylindrical recesses defined in an outer surface of the first end retainer, and a plurality of pressure ports extending from a corresponding one of the plurality of cylindrical recesses to the first rotary seal group, and a plurality of pistons slidably disposed in a corresponding one of the plurality of cylindrical recesses, wherein the pistons are exposed to the hydrostatic pressure.

10. The cutter assembly of claim 9, further comprising a plurality of extendable seals, wherein each extendable seal is attached near an outer edge of a corresponding one of the plurality of cylindrical recesses.

11. A pressure-compensated cutter assembly for a tunnel boring machine comprising:
a shaft;
a cutter ring assembly rotatably mounted on the shaft;
a first end retainer non-rotatably attached to one end of the shaft and a second end retainer non-rotatably attached to an opposite end of the shaft;
a first rotary seal group having a first portion engaging the cutter ring assembly and a second portion engaging the first end retainer; and
a second rotary seal group having a first portion engaging the cutter ring assembly and a second portion engaging the second end retainer;
wherein the first and second rotary seal groups are enclosed within a closed volume defined by the shaft, the cutter ring assembly, and the first and second end retainers, and further wherein the closed volume is otherwise filled with a lubricant; and
wherein the first end retainer includes a movable portion having an outer surface that is exposed to an ambient pressure and an inner surface exposed to the lubricant such that the movable portion will increase the pressure of the lubricant in response to an increase in the ambient pressure;
wherein the first end retainer comprises a fixed retainer having at least one pressure port that is in fluid communication with the lubricant, and the movable portion comprises a floating retainer that slidably engages the fixed retainer such that a gap is defined between the fixed retainer and the floating retainer, wherein the gap is filled with the lubricant; and
wherein the fixed retainer further comprises an annular channel and an outer perimeter, and further wherein the floating retainer comprises an annular wall that slidably engages the annular channel and an outer wall that slidably engages the outer perimeter of the fixed retainer.

12. The pressure-compensated cutter assembly of claim 11, wherein the floating retainer further comprises at least one through port to facilitate injecting lubricant into the gap.

13. The pressure-compensated cutter assembly of claim 11, wherein the cutter ring assembly comprises a hub rotatably mounted to the shaft with tapered roller bearings and a cutter ring extending radially outwardly from the hub.

14. The pressure-compensated cutter assembly of claim 11, wherein the first rotary seal group comprises a duo-cone seal.

15. A pressure-compensated cutter assembly for a tunnel boring machine comprising:
a shaft;
a cutter ring assembly rotatably mounted on the shaft;
a first end retainer non-rotatably attached to one end of the shaft and a second end retainer non-rotatably attached to an opposite end of the shaft;
a first rotary seal group having a first portion engaging the cutter ring assembly and a second portion engaging the first end retainer; and
a second rotary seal group having a first portion engaging the cutter ring assembly and a second portion engaging the second end retainer;
wherein the first and second rotary seal groups are enclosed within a closed volume defined by the shaft, the cutter ring assembly, and the first and second end retainers, and further wherein the closed volume is otherwise filled with a lubricant;
wherein the first end retainer includes a movable portion having an outer surface that is exposed to an ambient pressure and an inner surface exposed to the lubricant such that the movable portion will increase the pressure of the lubricant in response to an increase in the ambient pressure;
wherein the first end retainer comprises a fixed retainer having at least one pressure port that is in fluid communication with the lubricant, and the movable portion comprises a floating retainer that slidably engages the fixed retainer such that a gap is defined between the fixed retainer and the floating retainer, wherein the gap is filed with the lubricant; and wherein the first end retainer comprises an outer surface defining an annular channel with at least one pressure port that extends from the annular channel through the first end retainer and is in fluid communication with the first rotary seal group, and an annular piston slidably disposed in the annular channel and exposed to the ambient pressure, and further comprising means for retaining the annular piston in the annular channel.

16. The pressure-compensated cutter assembly of claim 15, wherein the at least one pressure port comprises a plurality of pressure ports.

17. The pressure-compensated cutter assembly of claim 15, wherein the at least one pressure port and the portion of the annular channel disposed inwardly of the annular piston are filled with the lubricant.

18. The pressure-compensated cutter assembly of claim 15, further comprising a retaining element disposed in the annular channel and operable to retain the annular piston in the annular channel.

19. A pressure-compensated cutter assembly for a tunnel boring machine comprising:
   a shaft;
   a cutter ring assembly rotatably mounted on the shaft;
   a first end retainer non-rotatably attached to one end of the shaft and a second end retainer non-rotatably attached to an opposite end of the shaft;
   a first rotary seal group having a first portion engaging the cutter ring assembly and a second portion engaging the first end retainer; and
   a second rotary seal group having a first portion engaging the cutter ring assembly and a second portion engaging the second end retainer;
   wherein the first and second rotary seal groups are enclosed within a closed volume defined by the shaft, the cutter ring assembly, and the first and second end retainers, and further wherein the closed volume is otherwise filled with a lubricant; and
   wherein the first end retainer includes a movable portion having an outer surface that is exposed to an ambient pressure and an inner surface exposed to the lubricant such that the movable portion will increase the pressure of the lubricant in response to an increase in the ambient pressure;
   wherein the first end retainer comprises a plurality of cylindrical recesses defined in an outer surface of the first end retainer, and a plurality of pressure ports extending from a corresponding one of the plurality of cylindrical recesses to the first rotary seal group, and a plurality of pistons slidably disposed in a corresponding one of the plurality of cylindrical recesses, wherein the plurality of pistons are exposed to the ambient pressure.

20. The pressure-compensated cutter assembly of claim 19, further comprising a plurality of extendable seals, wherein each extendable seal is attached near an outer edge of a corresponding one of the plurality of cylindrical recesses.

* * * * *

UNITED STATES PATENT AND TRADEMARK OFFICE
CERTIFICATE OF CORRECTION

PATENT NO. : 8,783,786 B2  Page 1 of 1
APPLICATION NO. : 13/397997
DATED : July 22, 2014
INVENTOR(S) : A. J. Shanahan et al.

It is certified that error appears in the above-identified patent and that said Letters Patent is hereby corrected as shown below:

| COLUMN | LINE | |
|---|---|---|
| item (57) Title page, col. 2 | Abstract 2 of text | after "shaft" insert --,-- |
| In the Claims | | |
| 9 Claim 15 | 2 | "filed" should read --filled-- |

Signed and Sealed this
Ninth Day of December, 2014

Michelle K. Lee
*Deputy Director of the United States Patent and Trademark Office*